United States Patent [19]

Bachmann

[11] Patent Number: 6,024,959
[45] Date of Patent: Feb. 15, 2000

[54] PHARMACEUTICAL COMPOSITION CONTAINING PECTIN AND A PHOSPHOLIPID USED AS AN ANTIDIARRHEAL AND ANTIULCER AGENT

[76] Inventor: Poul Bachmann, Demstrupvej 31, Randers, Denmark, DK-8900

[21] Appl. No.: 08/930,569

[22] PCT Filed: Apr. 3, 1996

[86] PCT No.: PCT/DK96/00168

§ 371 Date: Sep. 29, 1997

§ 102(e) Date: Sep. 29, 1997

[87] PCT Pub. No.: WO96/31239

PCT Pub. Date: Oct. 10, 1996

[30] Foreign Application Priority Data

Apr. 3, 1995 [DK] Denmark ................................ 0376/95

[51] Int. Cl.⁷ .......................... A61K 35/78; A61K 47/00; C08B 37/06
[52] U.S. Cl. .................... 424/195.1; 424/78.01; 424/439; 426/2; 426/615; 514/54; 514/867; 514/911; 536/2
[58] Field of Search ................................ 424/195.1, 439, 424/78.01; 514/54, 867, 911; 536/2; 426/2, 615

[56] References Cited

U.S. PATENT DOCUMENTS

| | | | |
|---|---|---|---|
| 4,076,717 | 2/1978 | Kreider | 546/194 |
| 4,162,306 | 7/1979 | Laves | 424/125 |
| 4,321,263 | 3/1982 | Powell et al. | 424/195.1 |
| 4,551,331 | 11/1985 | Rudin | 424/195.1 |
| 4,867,979 | 9/1989 | Sheth et al. | 424/195.1 |
| 4,950,655 | 8/1990 | Bachmann | 514/54 |
| 4,999,200 | 3/1991 | Casillan | 424/480 |
| 5,258,181 | 11/1993 | Cregier et al. | 424/195.1 |
| 5,462,742 | 10/1995 | Bogentoft et al. | 424/439 |

FOREIGN PATENT DOCUMENTS

WO 87/02243 4/1987 Denmark .
0 092 121 A1 4/1983 European Pat. Off. .

*Primary Examiner*—Leon B. Lankford, Jr.
*Assistant Examiner*—Christopher R. Tate
*Attorney, Agent, or Firm*—Watov & Kipnes, P.C.

[57] ABSTRACT

Agent for treatment and prevention of diarrhoea and gastric ulcers in animals and humans, consisting of a mixture of a pectinaceous plant fibre material with a phospholipid, said agent being obtained by adding to the plant fibre material prior to the admixture of phospholipid under intensive stirring a physiologically acceptable liquid organic substance having a surface tension which is significantly lower than that of water, and method of preparing said agent comprising mixing under intensive stirring the finely-milled, dried pectinaceous plant fibre material with 2 to 10% by weight of an organic substance based on the plant fibre material, preferably at least one alcohol, and subsequently adding under stirring from 5 to 15% by weight of lecithin based on the plant fibre material and heated to a temperature of more than 45° C. to obtain a homogeneous mixture.

18 Claims, No Drawings

PHARMACEUTICAL COMPOSITION CONTAINING PECTIN AND A PHOSPHOLIPID USED AS AN ANTIDIARRHEAL AND ANTIULCER AGENT

The present invention relates to a novel modified plant fibre preparation with a curative and prophylactic effect on acute infectious diarrhoea and chronic and subchronic, partially symptomless progressing diseases, including infections in the gastrointestinal tract.

Furthermore, the same preparation has surprisingly been found to have a curative effect on gastric ulcers.

Besides, the invention, which is a further development of DK patent No. 153,442 owned by the inventor, implies a substantial simplification of the manufacturing technique compared to that of the above DK patent.

It has long been known that plant fibres in general and in particular fibres having a high content of pectic substances (polygalacturonic acid complexes) exhibit a favourable effect on infectious and non-infectious diarrhoea.

Whereas the use of pectic substances previously rested on a purely empirical basis both within the popular medicine and in a more pharmaceutical-industrial connection, their effects today may be described as effects intervening in some of the pathophysiological mechanisms determining the development of the most widespread types of infectious diarrhoea.

Thus, numerous scientific investigations have demonstrated that the most widespread types of infectious diarrhoea, such as the enterotoxic *Escherichia coli* diarrhoea, and some virus-related types of diarrhoea are caused by disorders in the enzyme-related mechanisms which via the epithelium of the small intestine maintain a balance prevailing between liquid absorption and liquid secretion.

The disorder in the enteral liquid regulation caused by bacteria or virus infection typically results in a drastic reduction in the liquid absorption simultaneously with an excessive increase in the liquid secretion from the intestinal wall out into the bowel contents, which as a result of various self-increasing effects causes the development of diarrhoea.

It is generally known that these basic enzyme-related mechanisms of the diarrhoeic pathogenesis all require a prior adhesion of the pathogenic microorganisms to the outer cell layer of the intestinal epithelium, upon which the adhesion is quickly followed by a heavy bacterial proliferation. The adhesion followed by propagation, referred to as bacterial colonisation, is thus the first step of the diarrhoea-producing mechanisms described above.

As far as the pathogenesis of virus infections is concerned, it may be stated that the dysregulation of the liquid balance and the diarrhoea resulting thereof are caused by a damage of the epithelial cells associated with the virus infection.

Based on the above diarrhoeic pathogenesis, the latest patent literature contains descriptions of diarrhoeic agents which aim at intervening in the initial mechanisms decisive for the development of diarrhoea, the attention being particularly paid to the importance of hydrophobic/hydrophobic bonds, the so-called "like-like" interactions", e.g. for the development of *Escherichia coli* infections.

In order to intervene in some of the forces applying to the bacterial colonisation, EP patent publication No. 0 021 230 describes an agent comprising one or more polymeric carbohydrates or sugars having a hydrophobic group and a molecular weight which is sufficiently high to prevent them from penetrating a cellular membrane, and a physiologically acceptable inorganic material having a hydrophobic surface layer.

The purpose of using said combination of a polymer having a hydrophobic group and an inorganic material having a hydrophobic surface layer is to attract the pathogenic bacteria and to cause these to adhere to the polymer and the inorganic material rather than to the cell tissue, e.g. the intestinal cell tissue. The prior art agent does not contain pectin and the introduction of the hydrophobic group on the polymer is based on a chemical reaction, viz. an etherification, esterification or amidation.

DK patent No. 153 442 B belonging to the Applicant describes an agent based on a pectinaceous material for the treatment and prevention of diarrhoea in humans and animals, which agent is characterized in further comprising an amphophilic substance containing a long-chained hydrophobic group for increasing the effect of the pectinaceous material. The agent is characterized in that the amphophilic substance is lecithin.

Both patents mentioned maintain that the effect is attributable to an active intervention in the hydrophobic bonds between hydrophobic bacterial capsule antigens (adhesins, hydrophobins) and corresponding hydrophobic structures in the cell walls of the intestinal epithelium which are considered to be of decisive importance for the development of the bacterial colonisation.

However, continued investigations have shown that other points of views may be adopted as to said mechanism of action, and that the product described in DK patent No. 153,442 B may be further improved, as said product, even though its curative and prophylactic effect on infectious diarhoea have been demonstrated through treatment of several million calves, suffer from certain drawbacks, among which the following should be emphasized:

The effect on acute infectious diarrhoea in pigs is not satisfactory.

Aqueous suspensions of the agent are not sufficiently stable.

Both drawbacks are remedied with the present invention which consists of an agent for treatment of diarrhoea and gastric ulcers in animals and humans, said agent comprising a mixture of a pectinaceous plant fibre material with a phospholipid, characterized in that said agent is obtained by adding to the plant fibre material prior to the admixture of phospholipid under intensive stirring a physiologically acceptable liquid organic substance having a surface tension significantly lower than that of water. The agent according to the invention simultaneously provides a clinical effect also in case of symptomless progressing intestinal infections of a subchronic type, such as e.g. in case of Salmonella disease carrier states among poultry and pigs.

For both of the mentioned categories of intestinal infections it strongly applies that the affections associated with the bacterial colonisation are found not only in the anterior sections of the small intestine but also in the posterior sections thereof and in the colon.

This implies that an agent directed towards combatting these infections should possess a colloidal stability and activity which are sufficiently high to maintain the interfering effect of the colonisation for a maximum extent through the intestinal tract.

Moreover, it is of decisive importance that after suspension in the aqueous phase of the bowel contents the agent is quickly combined with said phase under the simultaneous formation of a gel.

Laboratory tests and clinical investigations have shown that surprisingly said problems can be remedied with the particular method of the present invention, which method consists in that prior to the mechanical mixture with lecithin the pectic fibres are conditioned with a physiologically acceptable organic liquid which contributes to increase the interface potential toward the aqueous phase and simultaneously makes the fibres more available to the lecithin.

Said liquid is preferably selected among alcohols, such as ethanol, glycerol, propylene glycol, polypropylene glycol, polyethylene glycol and mixtures thereof.

It has been found that a non-toxic monohydric alcohol, ethanol, a trihydric alcohol, glycerol or mixtures of these are particularly suitable as a physiologically acceptable, liquid organic substance having a surface tension lower than that of water.

It is preferred that the alcohol used is not removed again, but that it forms an integrated component of the finished product.

Besides, pyrrolidone-containing compounds, incl. polyvinyl pyrrolidone (PVP), may be used as a physiologically acceptable liquid organic substance. Polyvinyl pyrrolidone may be used in an aqueous solution at a concentration of 3–5% (w/w).

The organic substance may also be ethoxylated sorbitan fatty acid esters, which compounds are also known as polysorbates and Tween compounds. The ethoxy moiety of the compounds may be the polyoxy ethylene, and the fatty acid moiety may be $C_3$–$C_{18}$ fatty acids and derivatives thereof, preferably lauric acid, palmitic acid, stearic acid, and oleic acid.

The ethoxylated sorbitan fatty acid esters may be used alone or in combination with cellulose or a derivative thereof, such as methyl cellulose.

Finally, the organic substance may be comprised of a mixture of two or more of the above mentioned substances. A mixture of an alcohol and an ethoxylated sorbitan fatty acid ester is preferred due to their mutually promoting effects.

The organic substance may be used together with a promoter which enhances the above mentioned effect. Examples of such a promoter are mono- or diesters of propylene glycol and edible fatty acids.

A preferred embodiment of the invention uses a pectinaceous plant fibre material selected among potato pulp, citrus residues, apple residues, soya bean fibres, and similar materials constituting from 65 to 90% by weight of the finished mixture, and the alcohol used is ethanol or a mixture of ethanol and glycerol constituting from 2 to 10% by weight of the finished mixture based on the plant fibre material, and the phospholipid is any physiologically acceptable lecithin constituting from 5 to 15% by weight of the finished mixture.

Furthermore, the invention relates to the use of the agent defined in claims 1–4 for treating disorders associated with the alimentary tract in animals and humans, in particular disorders caused by Salmonella infection in the intestinal tract in mammals and birds, preferably chickens, pigs and calves, and gastric ulcers in mammals, in particular belonging to the unguinae order, and humans.

Finally, the invention relates to a feedstuff, preferably containing from 2 to 10% by weight of the agent according to the invention. A typical chicken feedstuff composition is 19% by weight of soya meal, 15% by weight of rapeseed, 33% by weight of wheat, 21% by weight of peas, 4.6% by weight of meat-and-bone meal, 2.6% by weight of fat, 1.8% by weight of minerals and vitamins, and 3.0% by weight of the agent according to the invention.

In order to obtain a partial simulation of the effect of diffently made preparations with regard to dispersion through the bowel content and of the effect with regard to physical influence on the consistency of the bowel content, comparative rheological tests have been made, in which the effects of the agent of the invention composed according to example 1 below were compared with the effects of a corresponding, non-alcohol-enriched fibre product consisting of:

| | |
|---|---|
| dried potato pulp | 158 g |
| citrus residues | 50 g |
| silicium dioxide | 2 g |
| lecithin | 40 g |
| | 250 g |

Comparative rheological tests surprisingly show that a significant improvement of the effect of the pectin-lecithin mixture on the consistency of the bowel content is obtained with the agent according to the invention.

Thus, the effect obtained with the improvement is that the conditioning of the pectic fibres with an alcohol mixture effected in accordance with the invention causes the fibres to combine momentarily with the bowel content under the formation of a homogeneous, gelatinaceous phase. After 8 hours this phase was found to be stable and showed no syneresis (liberation of water).

A similar rheological effect could not be obtained by mixing the bowel content with the corresponding non-alcohol-treated pectic fibre preparation, as said preparation showing no gelatinaceous properties would only be allowed to be combined with the bowel content under intensive mechanical influence.

The observed rheological effect, which is of a surprising nature, is important also in therapeutic connections, as it reflects a desired colloidal-chemical modification of the micro-structures to which adhesive potentials in respect of colonized bacteria cells may be attributed ipso facto.

Furthermore, continued comparative tests have shown that the preparation conditioned with alcohol is much more suspendable than the non-conditioned preparation.

Whereas the analogous, non-pretreated pectin-phospholipid mixture after stirring into water is quickly precipitated as a coherent mass, the alcohol conditioned product is kept floating in the liquid as an evenly distributed phase of agglomerated, macroscopically visible particles.

The invention will now be further illustrated by a number of examples.

EXAMPLE 1

| A mixture is prepared of: | | |
|---|---|---|
| dried potato pulp | | 150 g |
| citrus residues | | 50 g |
| ethanol 99% v/v | 5 g | |
| | | 10 g |
| glycerol | 5 g | |
| lecithin | | 40 g |
| | | 250 g |

After mechanical mixing of the two fibre products, potato pulp and citrus residues, the two mixed alcohols are added to the mixture. In this connection it is noted that the volume of the fibres is reduced. Lecithin heated to 45° C. is added after intensive mechanical stirring. Effective mixing of lecithin with the alcohol conditioned fibres is then obtained within a few minutes by continued mechanical stirring.

EXAMPLE 1.-B

Milled, dried citrus residues (A/S Københavns Pektinfabrik—having a water content of 12% and an average particle size of 0.5 mm) are mixed under intensive mechanical stirring with 4% by weight of an equal mixture of ethanol (99%/surface tension: 22.3 mN/m) and glycerol.

After completion of the mixing, which is characterized by a reduction of the volume of the fibre substance by about 15%, the method for condensation with lecithin defined in DK patent No. 153,442 B is carried out.

The product made, Mixture A, is compared by carrying out comparative Langmuir-Adam measurements and H.I.C. tests with a non-alcohol-enriched but otherwise identical pectinlecithin mixture, Mixture B, to which a granulation agent is added (technical additive).

In carrying out these tests a Langmuir-Adam surface balance apparatus is used which registers the changes in the surface tension of water after application of the preparation on the surface of the water in terms of the measuring unit mN/m.

Similarly the bacterial cell adsorbing effect of each preparation was measured and registered by carrying out H.I.C. tests (Hydrophobic Interaction Chromatography).

Lanqmuir-Adam Surface Balance Methodology

The application of an insoluble, non-volatile organic substance to the surface of water having a relatively high surface tension ($\tau_0 = 72,8$ mN/m) results in either:

1: The formation of a compact drop leaving the remaining water surface pure, or
2: The formation of a monolayer film which is dispersed over the entire water surface due to the interactions between water and the substance concerned.

In other words, the formation and maintenance of a monolayer depend on the adhesive forces between water and the constituent molecules of the monolayer being stronger than the cohesive forces applying to the substance.

The formation of monolayers and the determining forces thereof are identical, irrespective of whether free water surfaces, i.e. water/gas surfaces, or interfaces between water and other separated phases, such as solid substances, oil or gel phases, are concerned.

The reduction of the interface tension exerted by the monolayer corresponds to the surface pressure of the monolayer: $\Pi$. The expanding pressure thereby produced thus counteracts the contracting tension of the pure water surface, which will always be very distinct due to the intimate bonds of the H-bridges.

$\Pi = \tau_0 - \tau$ $\tau_0$ = the tension of the pure surface.

$\tau$ = the tension relating to the interface monolayer.

According to Gibb's theory, changes in the surface tension of water, $\Delta\tau$, and the maintenance of this effect in time will thus reflect the adsorptive capacity and stability of the monolayer.

In the Langmuir-Adam apparatus the surface pressure exerted by the monolayer is determined directly by measurement of the horizontally acting force by which the monolayer affects a floating body placed in the monolayer/water interface, see "Lipid and Biopolymer Monolayers at Liquid Interfaces", Birdi K. S., p. 292, Plenum Press, New York, 1989.

H.I.C.-Tests

Hydrophobic Interaction Chromatography Measurement of Bacteria Cell Adsorbing Capacity In the H.I.C. test the capability of various pectin-lecithin preparations to bind strains of diarrhoea-producing bacteria is determined by eluation of a pectin-lecithin impregnated Octyl-Sepharose column with a suspension of bacteria cells in a predetermined concentration.

Following column eluation the eluate is subjected to a spectophotometric measurement in order thereby to determine the amount of bacteria cells retained on the column (% cells adsorbed).

| Mixture A | | Mixture B | |
|---|---|---|---|
| Citrus residues | 50 g | Citrus residues | 50 g |
| Ethanol/glycerol aa. p. | 2 g | Lecithin | 18 g |
| Lecithin | 18 g | Silicium dioxide* | 2 g |
| | 70 g | | 70 g |

*Granulation agent

The results of the measurements effected are shown in Table 1.

| | Mixture A. | Mixture B. |
|---|---|---|
| Langmuir-Adam (mN/m). | 43 mN/m | 8 mN/m |
| H. I. C. (% E. coli-cells adsorbed). | 96% | 54% |

The measuring results shown in Example 1-A state the average of double determinations.

Supplementary investigations of 10 diffently made preparations, carried out as concurrent Langmuir-Adam measurements and H.I.C. tests, all showed a clear congruity between mN/m-values (maximum interface potential) and H.I.C. results (maximum % of E. coli cells adsorbed to the column).

Thus, the tests indicate that the bacteria eliminating effects primarily may be attributed to the colloidal-chemical relating interface potentials.

EXAMPLE 2

In a clinical test with diarrhoeic pigs the curative effect of an agent prepared according to the present invention is compared with the effect of a corresponding agent, prepared without preconditioning of the pectic fibre substance with alcohol.

The test was carried out on a large specific-pathogen-free pig herd, where all diarrhoeic pigs are isolated in a separate section of the climatic housing section designed for weaning piglets, which provides the possibility of carrying out comparative treatment tests on a uniform animal herd.

According to microbiological investigations the diarrhoeic pigs can be characterized by infection with $E.coli$ 0149 K88, i.e. an $Escherichia\ coli$ strain having antigen 0149 which is characteristic of pig pathogenicity and adhesin K88 which is responsible for adhesive properties (pig specific capsule antigen). This strain is sensitive to colistinsulphate but resistant to most other antibiotics.

A total of 38 pigs are put in the isolated housing section. Criteria for admission: diarrhoea accompanied by poor growth.

The 38 diarrhoeic pigs are divided into 4 groups, to which 4 small housing sections are allocated with 9–10 pigs in each.

Groups 1 and 3 (18 pigs) are treated with the pectic fibre phospholipid preparation prepared according to the present patent application.

Groups 2 and 4 (20 pigs) are treated with a pectic fibre phospholipid preparation which is identical with the one used for groups 1 and 3 except that the pectic substance used therein is not pretreated with an ethanol-glycerol mixture, compare the composition of the two test preparations, Table 2.

TABLE 2

Test preparations for the treatment of:

| Component | Groups 1 + 3 | Groups 2 + 4 |
|---|---|---|
| Citrus residues | 222.0 g | 227.0 g |
| Potato pectin | 119.0 g | 124.0 g |
| Ethanol | 5.0 g | — |
| Glycerol | 5.0 g | — |
| Lecithin | 136.5 g | 136.5 g |
| Electrolyte glucose* | 512.5 g | 512.5 g |
| | 1,000.0 g | 1,000.0 g |

*Electrolyte-glucose mixture for momentary rehydration of diarrhoeic pigs, composed of: NaCl, NaHCO$_3$, KCl, citrate and glucose.

Table 2 Composition of test preparations with and without preconditioning with ethanol-glycerol mixture and application of said compositions for 4 test groups.

Both test preparations are stirred into water at 35 g per liter of water given to each group as drinking water ad libitum.

The pigs are checked 3 times daily, the number of pigs suffering from diarrhoea and the number showing reduced appetite being recorded each time.

The test is continued for 48 hours after which the treatment is discontinued.

The results of the comparative test of the two preparations are shown in Table 3.

TABLE 3

| Group No. Number of pigs | Number of pigs suffering from diarrhoea after number of hours: | | | | |
|---|---|---|---|---|---|
| | 0 | 8 | 24 | 32 | 48 |
| 1 + 3 (18) | 18 | 16 | 8 | 6 | 2 |
| 2 + 4 (20) | 20 | 20 | 16 | 15 | 12 |

As will appear from Table 3, the number of diarrhoeic pigs in Groups 1 and 3 are reduced to 8 after 24 hours. After 48 hours 16 pigs (88%) out of the pigs treated with a product prepared according to the present invention are cured of diarrhoea.

In groups 2 and 4, 16 out of 20 pigs are still suffering from diarrhoea after 24 hours. After 48 hours 8 pigs (40%) out of the pigs treated with a product prepared without preconditioning the pectic fibres, are cured.

EXAMPLE 3

For the treatment of Salmonella-infected chickens the following mixture is prepared:

| | |
|---|---|
| Dried potato pulp | 300 g |
| Ethanol | 30 g |
| Lecithin | 90 g |
| | 420 g |

Out of a *Salmonella typhimurium*-infected flock, 10 chickens are selected. After detection of *S. typhimurium* by bacteriological investigation of individual dropping samples, the chickens are put in the same house, as they are divided into two separate groups A and B.

Group A is fed with a standard broiler feedstuff, "Brun Rapsi", K.F.K., 23% crude protein.

Group B is fed with the same feed mixture, admixed with 3% of the above pectin-ethanol-lecithin preparation.

After 9 days all the chickens are killed and subjected to a bacteriological investigation.

The bacteriological investigation shows that the chickens of Group A are still infected with *S. typhimurium*.

Salmonella are not detected in the chickens of Group B.

EXAMPLE 4

For treatment of gastrointestinal disorders in horses the following mixture is prepared:

| | | |
|---|---|---|
| Dried potato pulp | | 1,000 g |
| Potato pectic fibres ("Potex") | | 500 g |
| Citrus residues | | 1,000 g |
| Ethanol | 75 g | } 150 g |
| Glycerol | 75 g | |
| Lecithin | | 600 g |
| Dried potato pulp | | 1,000 g |
| Apple residues | | 400 g |
| | | 4,650 g |

As exemplified below the preparation is used as a curative agent in single doses of 300 g against diarrhoea and ulcer diseases in full-grown horses.

Diarrhoeic states 4-year-old Trotting Stallion

Through half a year the stallion has suffered from a recurring diarrhoea with foul stool. He is very nervous and his performances on the track are poor. The stallion has repeatedly been treated with preparations of Lactobacillus and different antibacterial agents prescribed by the veterinary but there has been no improvement of his condition.

The treatment with the agent according to the present invention is carried out twice at an interval of 10 days.

In each treatment 3×300 g are administered the first day followed by 300 g daily for 7 days. After the first treatment the diarrhoea had stopped, and the condition of the horse had significantly improved. When the horse again had mild outbreaks of diarrhoea and showed nervous symptoms on the track, the same treatment was repeated 10 days later. After two months there has been no recurrence of diarrhoea and the performance of the horse is now very satisfactory.

7-year-old Riding Horse

The horse, which is regularly used in competitions, has suffered from foul diarrhoea and at the same time extreme nervousness through several months. It has been treated repeatedly with preparations of Lactobacillus, various obstipantia and other agents prescribed by the veterinary without any change in the condition.

A treatment with the present agent, prescribed by the general veterinary, and administered at 3×300 g the first day followed by 300 g daily for 8 days, caused a permanent disappearance of all symptoms. The horse has been symptom-free for 3 months.

Gastric Ulcers

According to recent investigations in this country and abroad gastric ulcers are a frequently occuring disease in trotting horses and other horses which are used regularly in competitions.

Symptoms of the disease are typically:

The appetite of the horse is noticeably reduced, it eats the feedstuff in small portions, as it exhibits signs of a mild colic after each short feedstuff intake, it then returns to the trough, eats a small portion, becomes uneasy, etc. Without being really emaciated the horse is thin with taut belly, mat pelt layer and lack-lustre, sunken eyes. The horse is nervous, stressed and its performances on the track are extremely poor.

"Sleipner" a 5-year-old Trotting Stallion

The stallion, which initially had been sold for slaughtering due to his poor performances, is purchased for DKK 5,000 and stabled at a stud farm in Northern Jutland.

Symptomatic of ulcer diseases the stallion exhibits: mild attacks of colic in connection with each feedstuff intake, he eats the feedstuff in small portions with many intermissions. The horse is lean having a mat pelt layer. His performances are extremely poor: trots 800 m at a maximum.

After 10 days of treatment with the agent according to the invention the stallion is symptom-free; he eats normally and shows no signs of colic or the stress associated therewith.

After 2 months' training the stallion is chosen to participate in Dansk Travderby where he is proclaimed favorite candidate to win after having won the preliminary race. Owing to a virus-related tonsillitis attack 2 days before the race he ends up as No. 4 in the 1994 Derby race. Subsequently the horse wins several races in the summer of 1994.

There is a total of 29 registered treatments of similar cases with trotting horses. All treatments carried out by general veterinaries or by professional trainers resulted in a complete cure, irrespective of whether actual diarrhoea or as in most cases ulcer diseases were involved.

Treatment of Calves 26 calves having symptoms of gastric ulcers were treated with the preparation described above. Positive treatment results were registered in all cases.

EXAMPLE 5

Two recently acquired calves, about 8 weeks old, which are admitted into a particular fattening calf herd exhibit characteristic symptoms of gastric ulcers 1 week after the admission.

Both calves are emaciated. They are feeble and their urge to drink and eat is strongly reduced. The calves are non-febrile; there are no symptoms of pulmonary diseases and they do not suffer from diarrhoea.

Auscultation shows that the bowel activity is impaired. Both calves are distended in the right flank in which clear plashing sounds can be detected by deep palpation.

The calves are treated with a preparation consisting of:

| | |
|---|---|
| Dried potato pulp | 1,000 g |
| Potato pectic fibres ("Potex") | 500 g |
| Citrus residues | 1,000 g |
| Aqueous solution of Polyvinyl pyrrolidone ("Polyvidon DLS 86") 5% (w/w) | 200 g |
| Lecithin | 600 g |
| Dried potato pulp | 1,000 g |
| Apple residues | 400 g |
| | 4,700 g |

The agent is administered at a dosage of 2×50 g per day for 3 days followed by 1×50 g per day for 8 days.

After 2 days the distention of the right flank is reduced, the calves begin to drink milk replacer, the appetite is increased, and the condition gradually returns to normal within the next week.

Gastric ulcers are a typical chronic disease; it is therefore important that the treatment is continued throughout the entire period in order to prevent relapses.

EXAMPLE 6

Three calves of the same particular slaughter calf herd and having the same symptoms of gastric ulcers as those mentioned in example 5, are treated with a preparation composed of:

| | |
|---|---|
| Dried potato pulp | 1,000 g |
| Potato pectic fibres ("Potex") | 500 g |
| Citrus residues | 1,000 g |
| Aqueous solution of "Methyl cellulose M 20" 0.5% (w/w) and "Tween 60" 1.0% (w/w) | 120 g |
| Lecithin | 600 g |
| Dried potato pulp | 1,000 g |
| Apple residues | 400 g |
| | 4,620 g |

The treatment which is instituted at 2×50 g per day for 3 days followed by 1×50 g per day for 8 days resulted in full restitution.

I claim:

1. A composition for the treatment of diarrhea or gastric ulcers in animals and humans comprising a mixture of a) a pectinaceous plant fiber material in an amount of from 34 to 90% by weight based on the weight of said mixture combined with from 2 to 10% by weight based on the weight of the plant fiber material of a physiologically acceptable liquid organic substance having a surface tension no greater than that of glycerol and b) a phospholipid in an amount of from 5 to 40% by weight based on the weight of said plant fiber material.

2. The composition according to claim 1, wherein the organic substance is at least one alcohol.

3. The composition according to claim 2 wherein the alcohol is selected from the group consisting of ethanol, glycerol and mixtures thereof.

4. The composition according to claim 1, wherein the organic substance is a pyrrolidone-containing compound.

5. The composition according to claim 4, wherein the organic substance is polyvinyl pyrrolidone (PVP).

6. The composition according to claim 1, wherein the organic substance is an ethoxylated sorbitane fatty acid ester.

7. The composition according to claim 1 wherein the pectinaceous plant fiber material is selected from the group consisting of potato pulp, citrus residues, apple residues and soya bean fibers.

8. The composition according to claim 1 wherein the pectinaceous fiber material is from 65 to 90% by weight of the mixture.

9. The composition according to claim 1 wherein the phospholipid is lecithin.

10. The composition according to claim 1 wherein the amount of the phospholipid is from 5 to 15% by weight based on the weight of the plant fiber material.

11. A method of treating diarrhea in an animal or human comprising administering to the animal or human a diarrhea treating effective amount of the agent of claim 1.

12. A method of treating gastric ulcers in an animal or human comprising administering to the animal or human a gastric ulcer treating effective amount of the agent of claim 1.

13. The composition of claim 1 wherein the surface tension of the liquid organic substance is no lower than that of ethanol.

14. A feedstuff for the treatment of diarrhea and gastric ulcers comprising a mixture of a a) a feed and b) an effective amount of a composition comprising a mixture of:

i) a pectinaceous plant fiber material in an amount of from 34 to 90% by weight based on the weight of said mixture combined with from 2 to 10% by weight of a physiologically acceptable liquid organic substance having a surface tension no greater than that of glyclerol, and ii) a phospholipid in an amount of from 5 to 40% by weight based on the weight of said mixture.

15. The feedstuff of claim 14 wherein the surface tension of the liquid organic substance is no lower than that of ethanol.

16. A method of preparing a composition for the treatment of diarrhea or gastric ulcers comprising mixing an effective amount of a finely-milled, dried pectinaceous plant fiber material with from 2 to 10% by weight based on the weight of the plant fiber material of a liquid organic substance having a surface tension significantly lower than that of water to form a first mixture, combining the first mixture with from 5 to 15% by weight based on the weight of the plant fiber material of lecithin under stirring at a temperature of at least 45° C. to form said composition in the form of a homogenous mixture.

17. A feedstuff for the prevention of diarrhea comprising a mixture of a) a feed; and b) an effective amount of the composition comprising a mixture of (i) a pectinaceous plant fiber material in an amount of from 34 to 90% by weight based on the weight of said mixture combined with from 2 to 10% by weight of a physiologically acceptable liquid organic substance having a surface tension no greater than that of glycerol and (ii) a phospholipid in an amount of from 5 to 40% by weight based on the weight of said plant fiber material.

18. The feedstuff of claim 17 wherein the surface tension of the liquid organic substance is no lower than that of ethanol.

* * * * *